United States Patent [19]

Spano et al.

[11] Patent Number: 5,800,459
[45] Date of Patent: Sep. 1, 1998

[54] ELECTRIC FIELD CONTROL OF EPILETIFORM ACTIVITY

[75] Inventors: Mark L. Spano, Laurel; Steven J. Schiff, Rockville, both of Md.; Bruce J. Gluckman, Arlington, Va.; William L. Ditto, Woodstock, Ga.

[73] Assignee: The United States of America as represented by the Secretary of the Navy, Washington, D.C.

[21] Appl. No.: 773,459

[22] Filed: Dec. 24, 1996

Related U.S. Application Data

[63] Continuation-in-part of Ser. No. 825,150, Mar. 26, 1997.
[51] Int. Cl.⁶ .................................................. A66N 1/40
[52] U.S. Cl. ........................... 607/2; 607/45; 607/898
[58] Field of Search ............................ 607/2, 45, 148; 128/898

[56] References Cited

U.S. PATENT DOCUMENTS 5,411,540  5/1995  Edell et al. ........................ 607/2
5,522,863  6/1996  Spano et al. ....................... 607/45
5,566,685  10/1996  Litovitz et al. ................... 128/898

FOREIGN PATENT DOCUMENTS 1593665  9/1990  U.S.S.R. ........................... A61N 1/36

*Primary Examiner*—William E. Kamm
*Assistant Examiner*—Carl H. Layno
*Attorney, Agent, or Firm*—John Forrest; Jacob Shuster

[57] ABSTRACT

A DC electric field is applied to brain tissue in parallel alignment with neurons thereof during periods of brief duration while the tissue is undergoing epileptic activity. The electric field is controllably changed in polarity and magnitude to modify such epileptic activity based on data obtained by recording such activity through electrodes that are isopotentially aligned within the electric field imposed on a slice of the brain tissue.

6 Claims, 4 Drawing Sheets

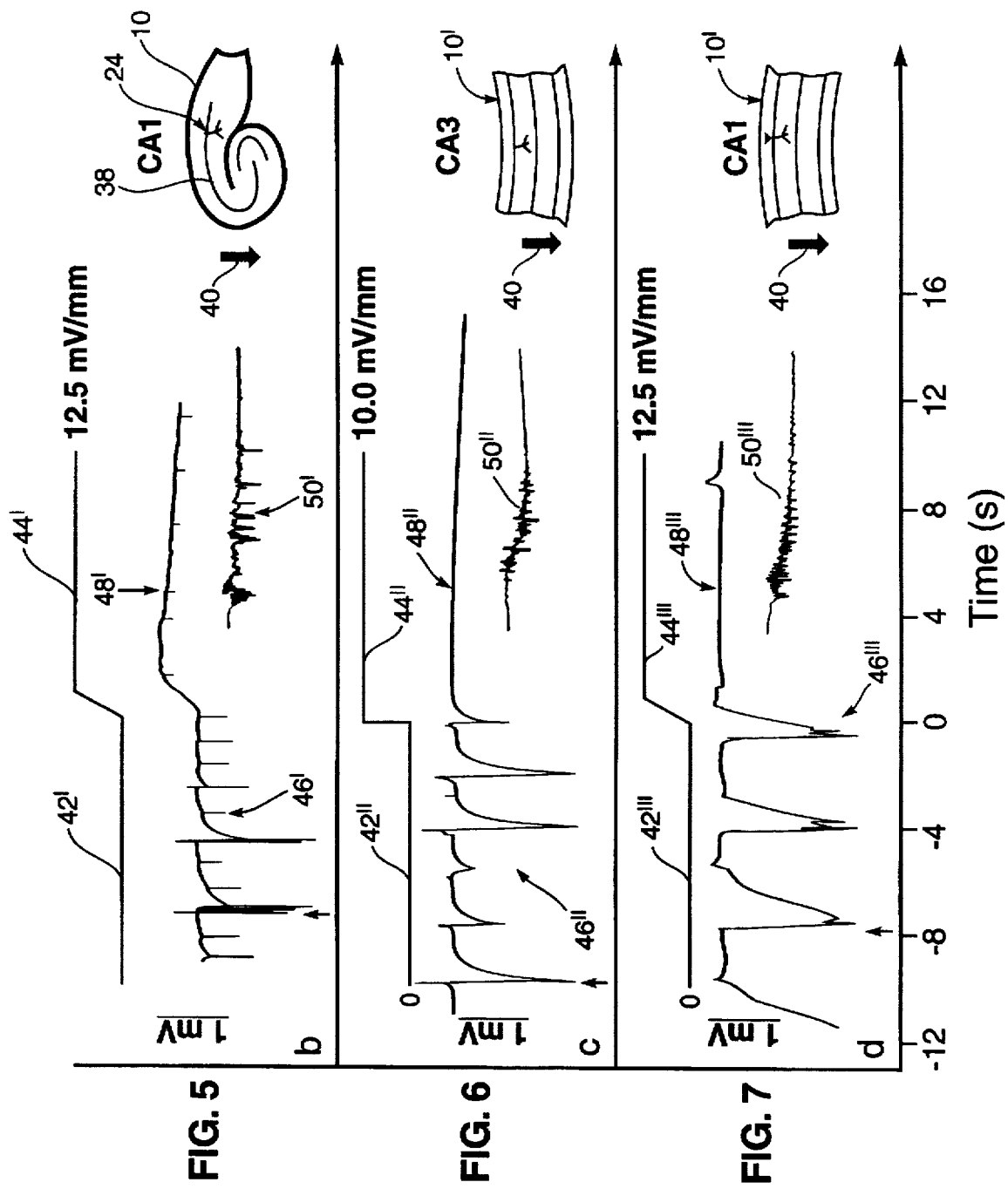

ELECTRIC FIELD CONTROL OF EPILETIFORM ACTIVITY

The present invention relates in general to the modification of activity in neuronal networks by use of electric fields externally applied thereto, and is related to subject matter covered in U.S. Pat. No. 5,522,863 which issued from an application copending with application Ser. No. 08/825,150 filed Mar. 26, 1997, with respect to which the present application is a continuation-in-part.

BACKGROUND OF THE INVENTION

It is already generally known in the art that electric fields affect neuronal excitability and that externally applied electric fields could suppress or enhance stimulus evoked neuronal activity. Experiments have also shown that injection of electric dc current into brain tissue could suppress evoked or spontaneous epileptiform activity. It has also been determined that an electric field aligned parallel to the dendritic-somatic axis of neurons within such brain tissue depolarizes the neurons to change the threshold for initiating action.

It is therefore an important object of the present invention to predictably modify epileptiform activity in biological tissue or the like by control over an externally applied electric field imposed on such tissue.

SUMMARY OF THE INVENTION

From studies performed on transverse and longitudinally cut hippocampal slices of brain tissue by recording synchronous activity from different regions, it was found that relatively small external DC electric fields will significantly affect such activity when locally imposed on the tissue aligned parallel with the dendritic-somatic axis of principal neurons of the neuronal network embodied in the brain tissue by changes in field polarity and magnitude. Neuronal activity at such regions in the tissue was monitored through recording and reference electrodes aligned along an isopotential within the electric field to provide data for suppression or enhancement of seizure-like events of the neuronal activity being monitored. Accordingly, a technique is established for non-invasive control of epilepsy by modifying seizure timings to achieve seizure suppression or prevention of seizure propagation, through generation and control of localized electric fields externally applied with appropriate orientation parallel to the neuronal dendrite-somatic axis. Thus, a method has been devised to control epileptic seizures with either minimal or no invasion.

BRIEF DESCRIPTION OF DRAWING FIGURES

A more complete appreciation of the invention many of its attendant advantages will be readily appreciated as the same becomes better understood by reference to the following detailed description when considered in connection with the accompanying drawing wherein:

FIGS. 5, 6 and 7 are graphical recordings such as those shown in FIG. 3 for different slice cuts of the brain tissue and different orientations of the electric field relative thereto.

DETAILED DESCRIPTION OF PREFERRED EMBODIMENTS

Figure 1:
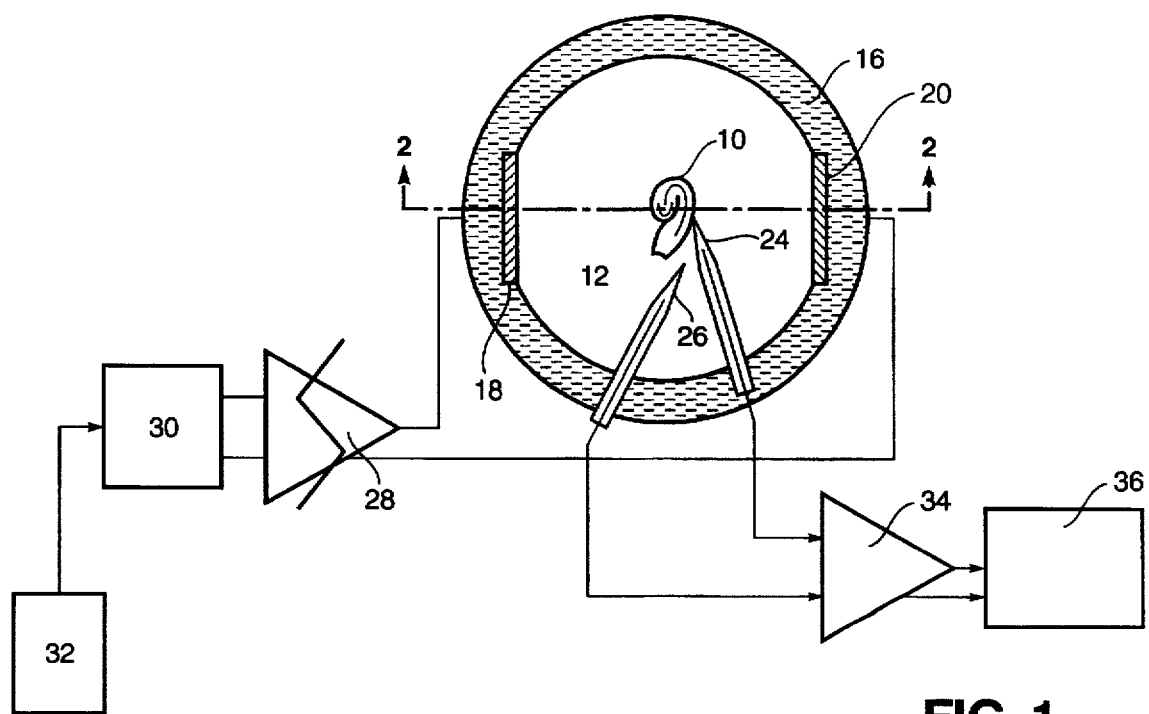
FIG. 1 is a partial top view and circuit diagram of an arrangement for inducing, recording and monitoring neuronal activity in a brain tissue slice.
Figure 2:
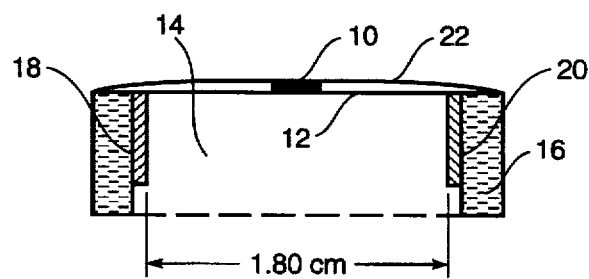
FIG. 2 is a partial section view taken substantially through a plane indicated by section line 2—2 in FIG. 1.

As disclosed in U.S. Pat. No. 5,522,863 to Spano et al., the disclosure of which is incorporated herein by reference, a slice of brain tissue obtained from the hippocompus of the temporal lobe, is perfused with a fluid containing potassium. The anatomy of the brain tissue includes a collateral fiber tract connected to pyramidal neurons of the Cornu Ammonis (CA) regions. The perfusate within which such brain tissue is submerged, is elevated in ionic concentration of the potassium to 8.5 mm in order to induce epileptic activity reflected by system characterizing events in the form of spontaneous burst firings and seizure-like events within the two regions (CA3 and CA1 respectively) at opposite ends of the collateral fiber tract. Such a brain tissue slice labeled by reference numeral 10 in FIGS. 1 and 2, is supported on a nylon mesh 12 submerged in artificial cerebrospinal fluid 14 as the perfusate within a chamber formed by an annular wall 16. A pair of parallel spaced (Ag-AgCl) electrode plates 18 and 20 are mounted by the wall 16 spaced from each other by 1.8 cm. for example. An electric field is established between the electrode plates 18 and 20 in the perfusion chamber within which the tissue slice 10 is centrally submerged in the body of perfusate fluid 14 adjacent to its upper surface 22 as shown in FIG. 2. A pair of saline filled glass micropipette electrodes 24 and 26 are shown in FIG. 1 for recording neuronal activity. The recording electrode 24 is positioned in the pyramidal cell layer of the brain tissue slice 10. The reference electrode 26 is adjustably spaced from electrode 24 within the perfusion chamber at a position along a field isopotential to minimize recording artifact by means of differential amplification. Such positional arrangement of the electrodes 24 and 26 allows for continuous recording of neuronal activity in the brain tissue slice 10 despite relatively substantial changes in the electric field established between the electrode plates 18 and 20.

With continued reference to FIG. 1, the electric field is externally imposed on the brain tissue slice 10 by applying a potential difference to the electrode plates 18 and 20 through a filtered stimulus isolation amplifier 28 driven by a digital-to-analog converter 30 connected to an electrical power source 32. Filtering in amplifier 28 removes high frequency artifacts introduced through digital to analog conversion of the input received from converter 30 and electrical isolation allows the differential potentials applied to the electrode plates 18 and 20 to "float" independently of ground. Isopotential measurement within the perfusion chamber, combined with neural layer identification, permits orientation and alignment of electric field with respect to the tissue slice 10. Both of the electrodes 24 and 26 are thereby positioned adjacent to the same measured isopotential in order to achieve continuous recording as aforementioned by connection through differential amplifier 34 to a recording monitor 36, as also diagrammed in FIG. 1, from which graphical data is obtained for use as hereinafter described.

Figure 3:
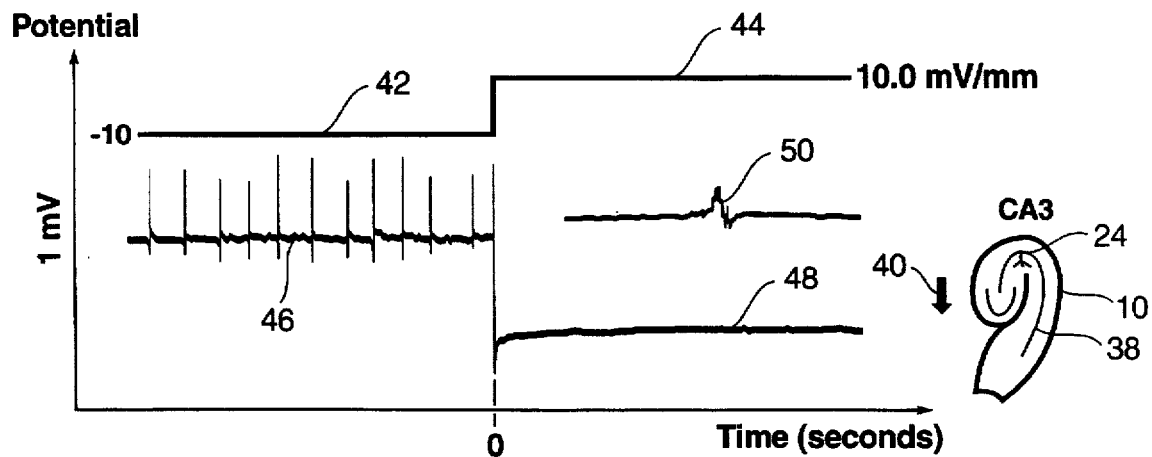
FIG. 3 is a graphical recording of electric field change and corresponding neuronal activity with respect to the brain slice shown in FIG. 1.

FIG. 3 graphically diagrams spontaneous neuronal activity with respect to a transversely cut brain tissue slice 10, based on data recorded through the electrode 24 shown positioned within the pyramidal cell body layer of the CA3 region of the tissue slice as shown by inset in FIG. 3. The tissue slice is also shown orientated with respect to a positive direction 40 of the electric field imposed thereon parallel to an axis extending from the soma to the apical dendrites of the neurons in the tissue being monitored. Such electric field when switched in polarity from negative level 42 to positive level 44 of 10 mv/mm as denoted in FIG. 3, effects an immediate suppression of spontaneous burst firing type of neuronal activity 46 in the tissue slice to a completely suppressed activity 48. A graphical inset in FIG. 3 of baseline activity 50 depicts one of the neuronal population bursts associated with activity 46 along an expanded time scale.

Figure 4:
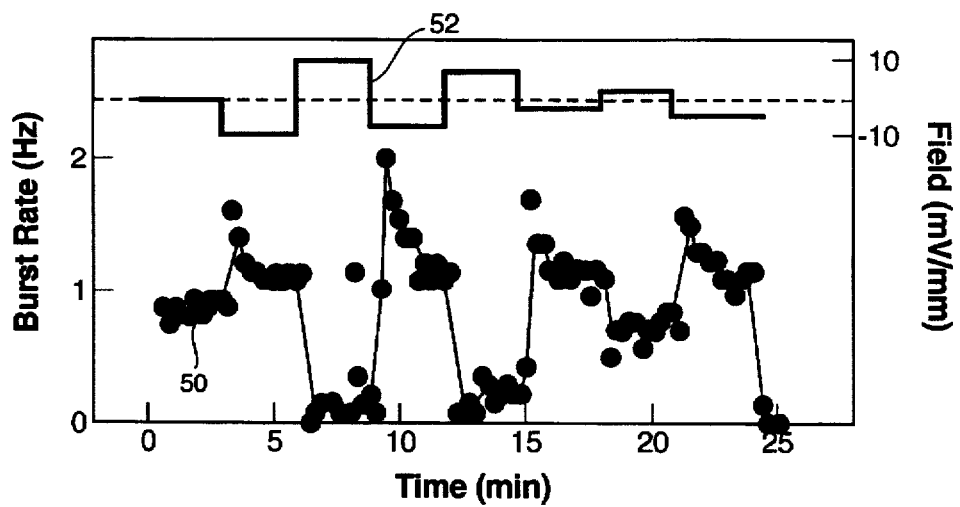
FIG. 4 is an enlarged graphical recording of the neuronal activity for the brain slice shown in FIG. 1, affected by graphically depicted polarity reversals and changes in field magnitude.

With either a zero level or no external electric field applied, a baseline neuronal activity 50 is exhibited within the tissue slice 10, as graphically depicted in FIG. 4. Such baseline activity 50 has a burst frequency of approximately one per second which is increased and decreased, as depicted by the graphical activity recordings 46 and 48, as a result of changes in field polarity corresponding to the graphical field level recordings 42 and 44 of equal magnitude. The relationship between both polarity and magnitude of the electric field on burst frequency of the neuronal activity in the CA3 region of the brain tissue slice 10, is reflected during alternative switching between negative and positive polarity of the externally applied electric field at different levels as depicted by the solid line graphical recording 52 in FIG. 4. The corresponding graphical recording 54 of burst rate in FIG. 4, reflects the effect of increased electric field magnitude in enhancing or suppressing activity excitation from the baseline activity depending on polarity.

Neuronal activity in brain tissue slices that differ in cut and orientation relative to the activity inducing electric field is depicted in FIGS. 5, 6 and 7. The neuronal activity graphically depicted in FIG. 5 is associated with a transversely cut tissue slice 10 orientated perpendicular to the field direction 40. Based on activity recording through electrode 24 positioned within the pyramidal cell body layer of the CA1 region, bursts 46' are suppressed to 48' by the electric field at positive level 44' of 12.5 mv/mm. Baseline activity 50' is also recorded in FIG. 5 at zero level electric field and expanded time scale.

When hippocampal brain tissue slices 10' are longitudinally cut as depicted in FIGS. 6 and 7, the pyramidal cells in the CA3 and CA1 regions are more uniformly aligned with the electric field direction 40 to more readily suppress from the activity 46" or 46'", in response to a change in field 42" or 42'" from zero, to the activity 48" or 48'" under the positive polarity field 44" or 44'". The graphical insets 50" and 50'" depict the baseline activity 46" and 46'" along an expanded time scale in FIGS. 6 and 7.

It will therefore be apparent from the foregoing description of recorded neuronal activity that relatively small dc electrical fields externally applied to tissue, aligned parallel to the direction of the apical dendritic-somatic axis of the pyramidal neurons consistently suppress seizure-like epileptiform activity, depending on field polarity, independently of the neuronal layer location and cut of the tissue slice. Further, neural activity is enhanced from the spontaneous baseline by polarity reversal of the applied electric field. Accordingly, an electric field may be externally applied with alignment and polarity control to neuronal networks, such as biological brain tissue, to modify epileptiform activity through an appropriate behavior modifying program based on reversal of polarity and change in magnitude of an electric field externally imposed.

Figure 8:
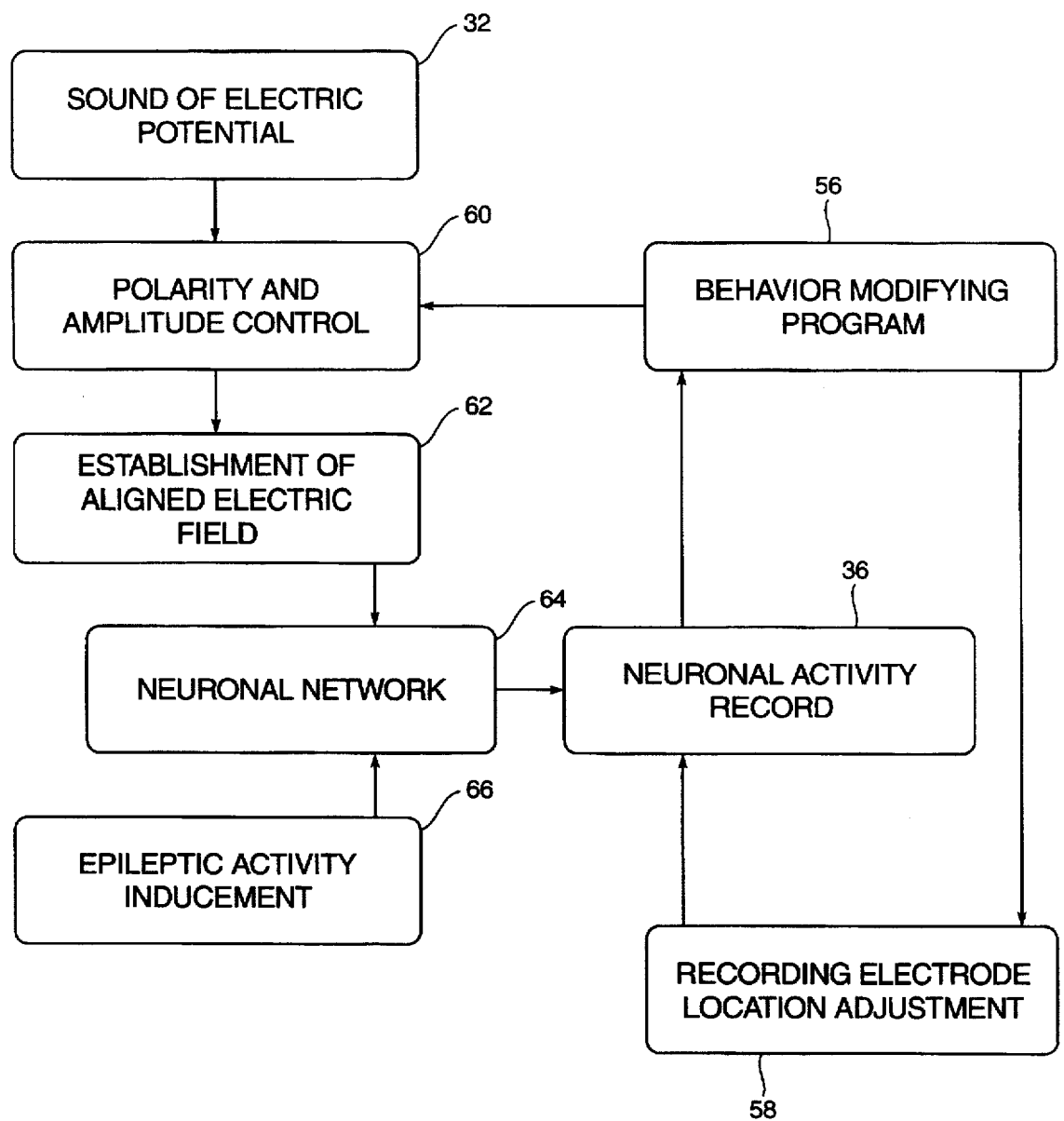
FIG. 8 is a block diagram of the activity modifying system associated with the present invention.

A behavior modifying program denoted by reference numeral 56, is diagrammed in FIG. 8 to outline the neuronal activity suppression and enhancement modification hereinbefore described. Such program 56 determines recording electrode location through adjustment 58 and field polarity and amplification control 60 of the electric potentials from source 32 as also denoted in FIG. 8. Establishment of the aligned electric field, denoted as 62 in FIG. 8, is thereby achieved with respect to a neuronal network 64 such as that embodied in the brain tissue slice 10 within which epileptic activity occurs spontaneously, or is induced as denoted by reference numeral 66. Such neuronal activity is monitored by the recordation monitor 36 through the recording electrodes 24 and 26 aligned along an isopotential as hereinbefore described to provide an input to the behavior modifying program 56 for control of epileptic focus, thereby suppressing or abolishing epileptic activity through dc electric fields of short duration.

Obviously, other modifications and variations of the present invention may be possible in light of the foregoing teachings. It is therefore to be understood that within the scope of the appended claims the invention may be practiced otherwise than as specifically described.

What is claimed is:

1. A method of modifying behavior of a neural system having a dendritic-somatic axis, including the steps of: generating an electric field; orientating the electric field in parallel with the dendritic-somatic axis of the neural system; and controlling reversal of polarity and changes in magnitude of the electric field to modify seizure-like events of epileptic activity in the neural system.

2. The method as defined claim 1, further including the step of; recording the epileptic activity in the neural system through isopotentially aligned electrodes to determine said changes in the electric field.

3. The method as defined in claim 2 wherein the neural system embodies brain tissue exposed to a perfusate through which the epileptic activity is induced.

4. The method as defined in claim 1 wherein the neural system embodies brain tissue exposed to a perfusate through which the epileptic activity is induced.

5. A method of modifying behavior of a neural system within which epileptic activity occurs including the steps of: generating an electric field; positioning the electric field in operative alignment with the neural system; recording the epileptic activity occurring in the neural system; and changing the electric field in polarity and magnitude dependent on said recording of the epileptic activity for modification of seizure-like events.

6. A method of treating pulsating activity of a neural system, including the steps of: monitoring behavior of the neural system by recordation of said pulsating activity through isopotentially aligned electrodes; applying an electric field to the neural system; and changing polarity and magnitude of the electric field in accordance with data obtained by said recordation through the electrodes.

* * * * *